United States Patent
Nelson et al.

(10) Patent No.: US 10,251,659 B2
(45) Date of Patent: Apr. 9, 2019

(54) COMPLIANT SURGICAL GRASPERS AND METHODS OF MAKING AND USING

(71) Applicant: NUTECH VENTURES, Lincoln, NE (US)

(72) Inventors: Carl Nelson, Lincoln, NE (US); Alan Goyzueta, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 818 days.

(21) Appl. No.: 14/390,124

(22) PCT Filed: Apr. 2, 2013

(86) PCT No.: PCT/US2013/034980
§ 371 (c)(1),
(2) Date: Oct. 2, 2014

(87) PCT Pub. No.: WO2013/152019
PCT Pub. Date: Oct. 10, 2013

(65) Prior Publication Data
US 2015/0119927 A1    Apr. 30, 2015

Related U.S. Application Data

(60) Provisional application No. 61/619,055, filed on Apr. 2, 2012.

(51) Int. Cl.
*A61B 17/29* (2006.01)
*A61B 17/00* (2006.01)
*A61B 90/00* (2016.01)

(52) U.S. Cl.
CPC .... *A61B 17/29* (2013.01); *A61B 2017/00296* (2013.01); *A61B 2017/00867* (2013.01); *A61B 2017/294* (2013.01); *A61B 2017/2926* (2013.01); *A61B 2017/2932* (2013.01); *A61B 2017/2937* (2013.01); *A61B 2017/2939* (2013.01); *A61B 2017/2944* (2013.01); *A61B 2017/2945* (2013.01); *A61B 2090/032* (2016.02); *A61B 2090/08021* (2016.02)

(58) Field of Classification Search
CPC ............ A61B 17/29; A61B 2017/2926; A61B 2017/2932; A61B 2017/2939; A61B 2017/294; A61B 2017/2944; A61B 2017/2945
See application file for complete search history.

(56) References Cited

U.S. PATENT DOCUMENTS

| | | |
|---|---|---|
| 5,538,008 A | 7/1996 | Crowe |
| 5,638,827 A | 6/1997 | Palmer et al. |
| 5,820,630 A | 10/1998 | Lind |

(Continued)

FOREIGN PATENT DOCUMENTS

| | | |
|---|---|---|
| WO | 96/00033 | 1/1996 |
| WO | 2001/082847 | 11/2001 |
| WO | 2006/098994 | 9/2006 |

OTHER PUBLICATIONS

DeVisser et al., "Forces and displacements in colon surgery," Surg. Endosc., 16:1426-30, Oct. 2002.

(Continued)

*Primary Examiner* — Robert Lynch
(74) *Attorney, Agent, or Firm* — Fish & Richardson P.C.

(57) ABSTRACT

This disclosure describes compliant graspers for use in endoscopic surgeries.

12 Claims, 8 Drawing Sheets

(56) References Cited

U.S. PATENT DOCUMENTS

| | | | |
|---|---|---|---|
| 6,206,877 B1 | 3/2001 | Kese et al. | |
| 6,964,662 B2 | 11/2005 | Kidooka | |
| 7,494,501 B2 | 2/2009 | Ahlberg et al. | |
| 8,864,795 B2 * | 10/2014 | Kerr | A61B 18/1442 606/167 |
| 2001/0021842 A1 | 9/2001 | Ouchi | |
| 2002/0133170 A1 * | 9/2002 | Tsuruta | A61B 17/221 606/127 |
| 2003/0171739 A1 * | 9/2003 | Murphy | A61B 17/12022 606/1 |

OTHER PUBLICATIONS

International Preliminary Report on Patentability and Written Opinion in International Patent Application No. PCT/US2013/034980, dated Oct. 7, 2014, 9 pages.

International Search Report and Written Opinion in International Patent Application No. PCT/US2013/034980, dated Jul. 18, 2013, 21 pages.

Marucci et al., "A compliant tip reduces the peak pressure of laparoscopic graspers," Australian and New Zealand J. Surgery, 72:476-478, Jul. 2002.

Sliker et al., "Micropatterned Treads for in Vivo Robotic Mobility," J. Med. Devices, 4:041006, Dec. 2010.

* cited by examiner

COMPLIANT SURGICAL GRASPERS AND METHODS OF MAKING AND USING

CROSS REFERENCE TO RELATED APPLICATIONS

This application is a National Phase application under 35 U.S.C. § 371 to International Application No. PCT/US2013/034980 having an International Filing Date of Apr. 2, 2013, which claims the benefit of priority under 35 U.S.C. § 119(e) to U.S. Application No. 61/619,055 filed Apr. 2, 2012, the disclosures of which are incorporated herein in their entirety.

TECHNICAL FIELD

This disclosure generally relates to surgical instruments.

BACKGROUND

During endoscopic surgery, soft tissues are grasped and stretched repeatedly, and excessive grasping force can cause unwanted tissue damage. With traditional endoscopic graspers, high pressures are applied to the tissue by the tip of the jaw, causing trauma. However, it has been shown that replacing a portion of the teeth at the tip of the jaw with a compliant material reduces the peak tip pressure during grasping (Marucci et al., 2002, Australian and New Zealand J. Surgery, 72:476-8).

The device described herein provides an inexpensive, fully compliant grasper capable of softly but firmly grasping tissue using a jaw made completely from a monolithic compliant member. By allowing the grasper to deform as it interacts with the tissue, the grasper can apply a more uniform pressure during grasping to, thereby, avoid unnecessary trauma.

SUMMARY

This disclosure describes compliant graspers for use in endoscopic surgeries.

In one aspect, an atraumatic grasper device is provided. Such a device typically includes a base having a proximal end, a distal end, and a longitudinal axis extending therebetween, where the proximal end of the base is configured to be releasably attached to a distal end of an endoscopic instrument. In addition, the distal end of the base generally includes a first grasping arm and an opposing second grasping arm, where each of the first and the second grasping arms are made from a compliant material and comprise a first end and a second end, where the first end of the first grasping arm and the first end of the second grasping arm are positioned distal to the longitudinal axis along a transverse axis and where the second end of the first grasping arm and the second end of the second grasping arm are positioned proximal to the longitudinal axis along the transverse axis. In this configuration, either the first ends of the first and second grasping arms or the second ends of the first and second grasping arms are moveable along the longitudinal axis and actuate atraumatic grasping of an object between the first and second grasping arms.

In another aspect, an endoscopic grasper device is provided. Such a device typically includes an elongate housing member having a longitudinal axis and having a handle at a proximal end, and opposing first and second grasping arms at a distal end. Generally, each of the first and the second grasping arms are made from a compliant material and comprise a first end and a second end, where the first end of the first grasping arm and the first end of the second grasping arm are positioned distal to the longitudinal axis along a transverse axis and where the second end of the first grasping arm and the second end of the second grasping arm are positioned proximal to the longitudinal axis along the transverse axis. In this configuration, either the first ends of the first and second grasping arms or the second ends of the first and second grasping arms are moveable along the longitudinal axis to actuate atraumatic grasping of an object between the first and second grasping arms.

In still another aspect, a method for atraumatically manipulating an object during an endoscopic procedure is provided. Such a method typically includes (a) providing an endoscopic grasper device that includes an elongate housing member having a longitudinal axis and a handle at a proximal end and opposing first and second grasping arms at a distal end, where each of the first and the second grasping arms are made from a compliant material and include a first end and a second end, where the first end of the first grasping arm and the first end of the second grasping arm are positioned distal to the longitudinal axis along a transverse axis and where the second end of the first grasping arm and the second end of the second grasping arm are positioned proximal to the longitudinal axis along the transverse axis. In this configuration, either the first ends of the first and second grasping arms or the second ends of the first and second grasping arms are moveable along the longitudinal axis to actuate atraumatic grasping of an object between the first and second grasping arms. Such a method also typically includes (b) introducing the distal end of the endoscopic grasper device into a patient; and (c) actuating the first and second grasping arms to atraumatically manipulate an object.

In some embodiments, the first and second grasping arms are made of shape memory alloy. In some embodiments, the compliant material is elastic material. In one embodiment, the first ends of the first and second grasping arms are moveable along the longitudinal axis, while in another embodiment, the second ends of the first and second grasping arms are moveable along the longitudinal axis.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

Like reference symbols in the various drawings indicate like elements.

DETAILED DESCRIPTION

This disclosure describes a unique grasper device for use with an endoscopic instrument. The approach described herein results in graspers that are deformable such that they have more uniformly distributed grasping forces and reduce the tissue trauma relative to conventional graspers.

Figure 1:
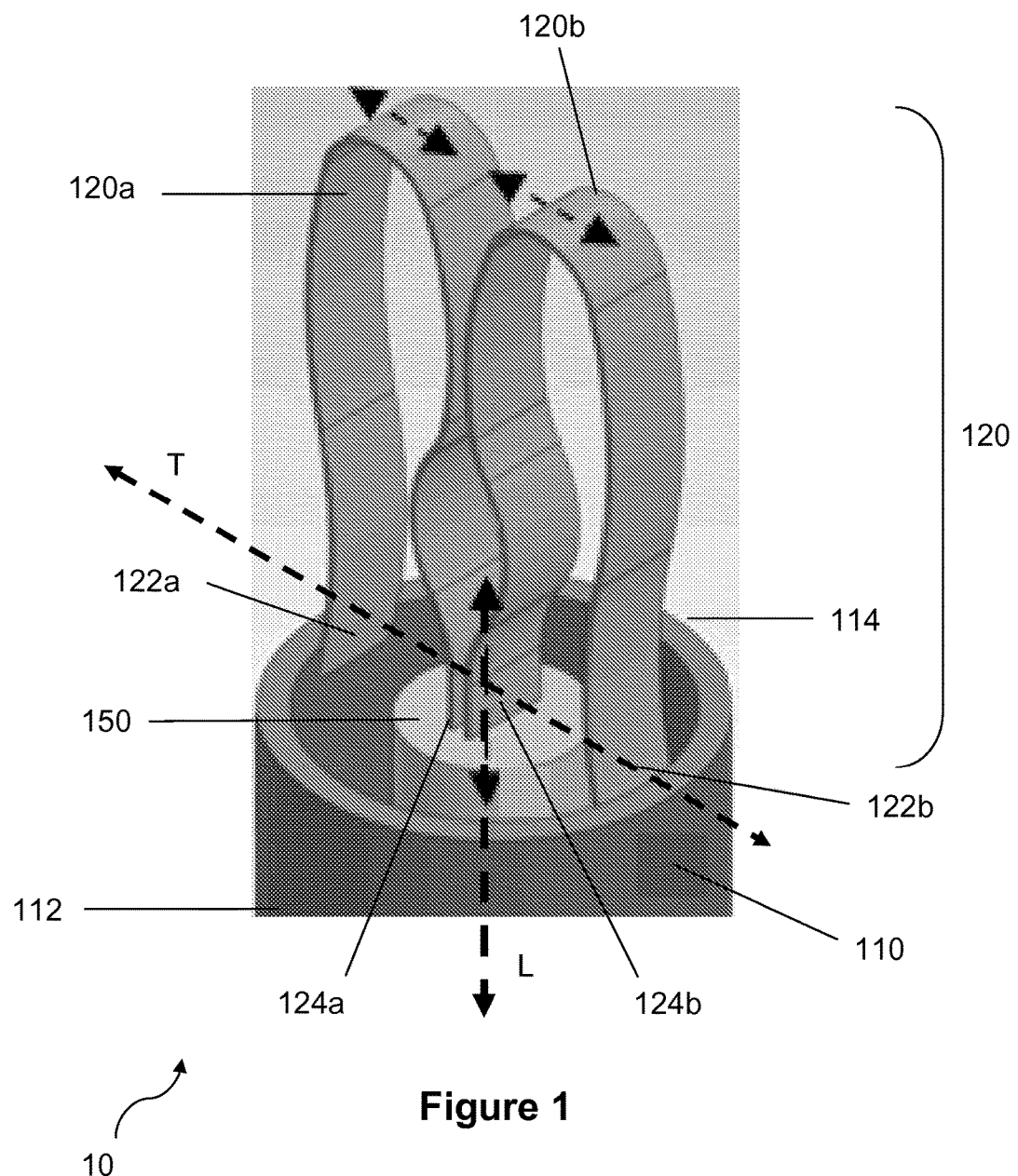
FIG. 1 is an image showing one embodiment of the compliant grasping arms as described herein.

FIG. 1 shows one embodiment of a grasper device 10. A grasper device as described herein typically includes a base 110 having a proximal end 112, a distal end 114, and a longitudinal axis L that extends therebetween. Those skilled in the art would appreciate that the proximal end 112 of a base 110 can be configured in any number of ways so as to be releasably attachable to the distal end of an endoscopic instrument (e.g., a laparoscope or an endoscope). Configurations for releasably attaching a grasper to an endoscopic instrument are known in the art and include, without limitation, snap-on or snap-fit attachments, latch or hook attachments, and slot or groove receiver with a corresponding flange.

The distal end 114 of the end effector base 110 includes atraumatic grasping arms 120 as described herein. FIG. 1 shows one configuration of a first grasping arm 120a and an opposing second grasping arm 120b in which a first end 122a of the first grasping arm 120a and a first end 122b of the second grasping arm 120b are positioned distal to the longitudinal axis L along a transverse axis T and a second end 124a of the first grasping arm 120a and a second end 124b of the second grasping arm 120b are positioned proximal to the longitudinal axis L along the transverse axis T. In the embodiment shown in FIG. 1, the first 120a and second 120b grasping arms are two distinct members, with the first ends 122 of each attached directly to the base 110 (i.e., distal to the longitudinal axis L along a transverse axis T) and the second ends 124 of each attached to a center member 150 (i.e., proximal to the longitudinal axis L along the transverse axis T).

As described herein, the grasping arms are made from a compliant material (e.g., elastic materials, superelastic materials, and/or deformable materials). Compliant materials are those that impart flexibility so as to accommodate the contours of the object while still allowing a firm grasp. Shape memory materials are routinely used and include, for example, shape memory alloys (e.g., nickel-titanium, copper-zinc-aluminum-nickel, or copper-aluminum-nickel) and/or rubber or thermoplastic elastomeric material (e.g., DYNAFLEX D-series (styrene-butadiene elastomer), DYNAFLEX G-series (styrene-ethylene/butylene-styrene copolymer), C-flex, SANPREN, silicone, or latex). An exemplary compliant shape memory material used routinely in medical devices is Nitinol, but other materials with similar compliant properties are suitable.

The physical size of the compliant material will depend upon the application; the material cannot be so small that it is not able to sufficiently and reliably grasp or manipulate the desired object, and the material cannot be too big (e.g., too wide and/or too thick) that it becomes non-compliant. Simply by way of example, wire-like compliant materials having a diameter of about 0.4 mm or greater (e.g., about 0.5 mm, 0.6 mm, 0.8 mm, 1 mm, or greater) can be used, or ribbon-like compliant materials having a thickness of about 0.2 mm or greater (e.g., about 0.3 mm, 0.5 mm, 0.8 mm, 1 mm or greater) and a width of about 3 mm or greater (e.g., about 5 mm, 8 mm, 10 mm or greater) can be used.

Any number of mechanisms can be utilized to move the graspers. Generally, either the first ends of both of the grasping arms are moveable in a direction corresponding to the longitudinal axis or the second ends of both of the grasping arms are moveable in a direction corresponding to the longitudinal axis. Due, at least in part, to the compliant nature of the grasping arms, this movement actuates and allows for the atraumatic grasping of an object (e.g., tissues, organs). The movement described herein provides for either a default-open position or a default-closed position, or for a default-intermediate position that is neither fully open nor fully closed.

Figure 2:
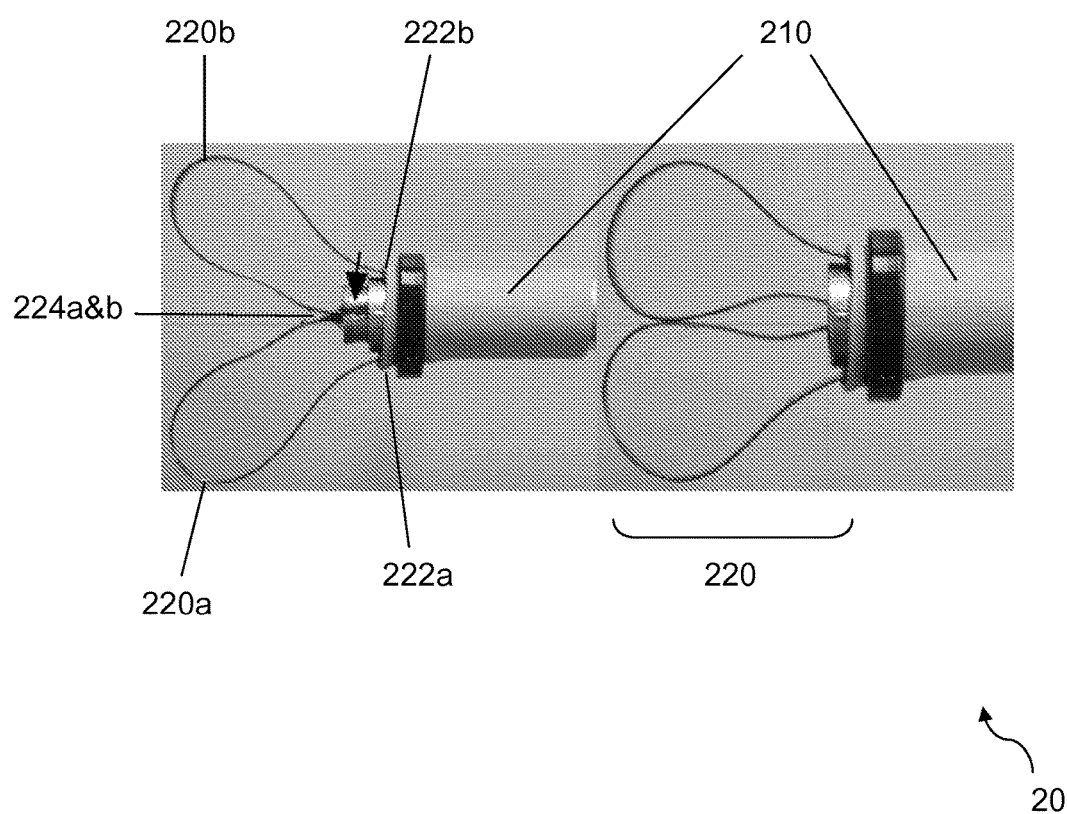
FIG. 2 is an image showing another embodiment of the compliant grasping arms as described herein in an open position (left panel) and closed position (right panel).

FIG. 2 shows another embodiment of a grasper device 20. The base 210 is shown, as well as the grasping arms 220. In the embodiment shown in FIG. 2, the second end 224a of the first grasping arm 220a is continuous with the second end 224b of the second grasping arm 220b and, similar to FIG. 1, grasping occurs by longitudinal L movement of the second ends 224 of both grasping arms 220, while the first ends 222 of both grasping arms 220 are fixedly attached to the base 210. Although both FIGS. 1 and 2 show movement of the second ends of both grasping arms, as indicated herein, movement of the first ends of both grasping arms is not precluded and would result in the same or functionally similar grasping action.

Figure 3:
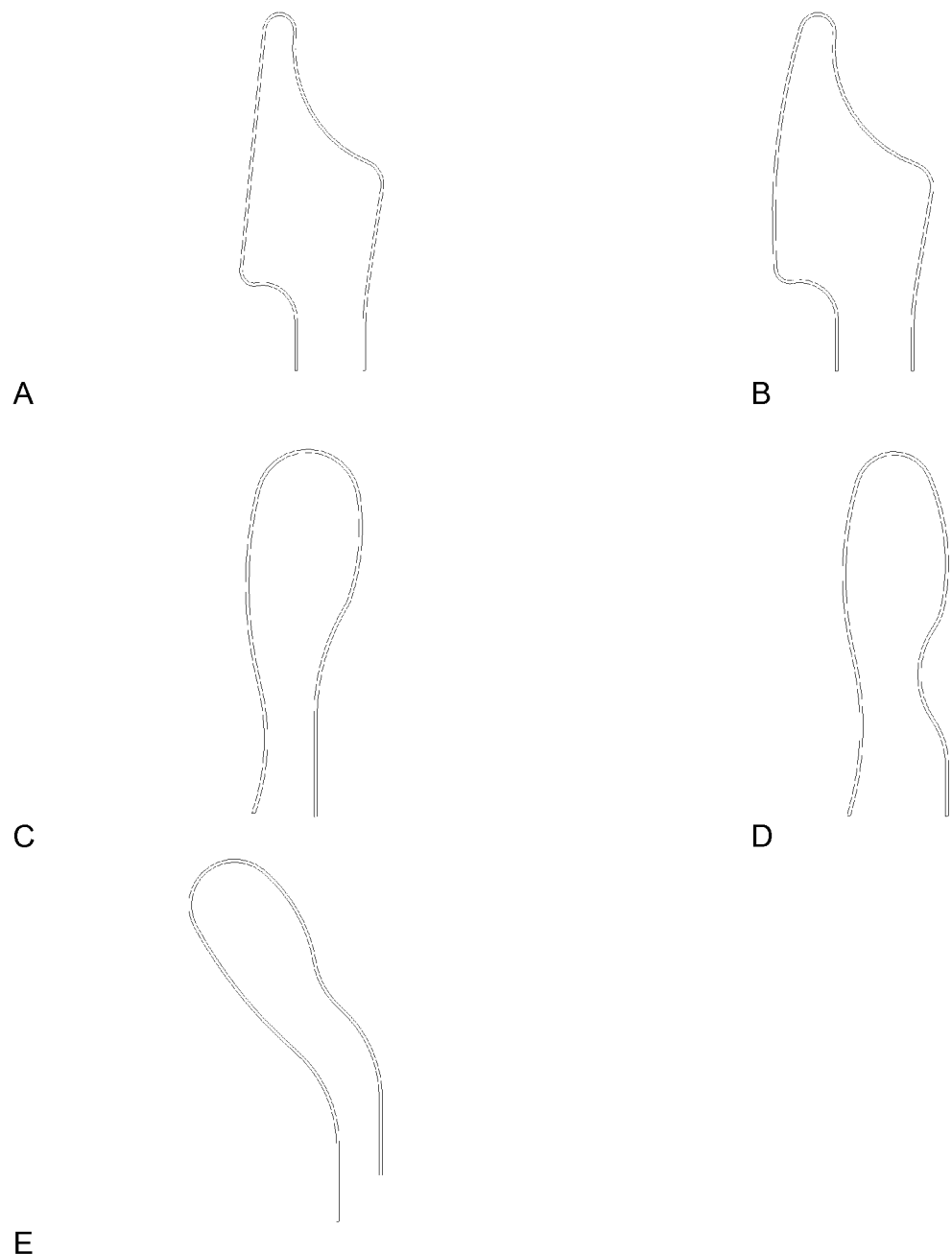
FIG. 3A-3E are images of suitable grasper arm profiles.

FIGS. 1 and 2 show different geometrical profiles for the grasping arms described herein. While it would be understood that virtually any profile can be used, it would be appreciated that certain profiles would be more atraumatic than others. Suitable shapes that can be incorporated into the profile of an atraumatic grasping arm as described herein include, without limitation, bumps, ribs, C-shape regions or portions, concave regions or portions, convex regions or portions, corrugated regions or portions, one or more depressions, sinusoidal regions or portions, serpentine regions or portions, and combinations thereof. The shapes of various regions or portions as well as the overall profile of the grasping arms will determine the degree of compliance of the arms, the amount of opening capable by the arms, and the pinch and pull forces that can be generated from such arms. FIG. 3 shows a number of different profiles of grasper arms that were found to exhibit positive kinematic performance.

Figure 6:
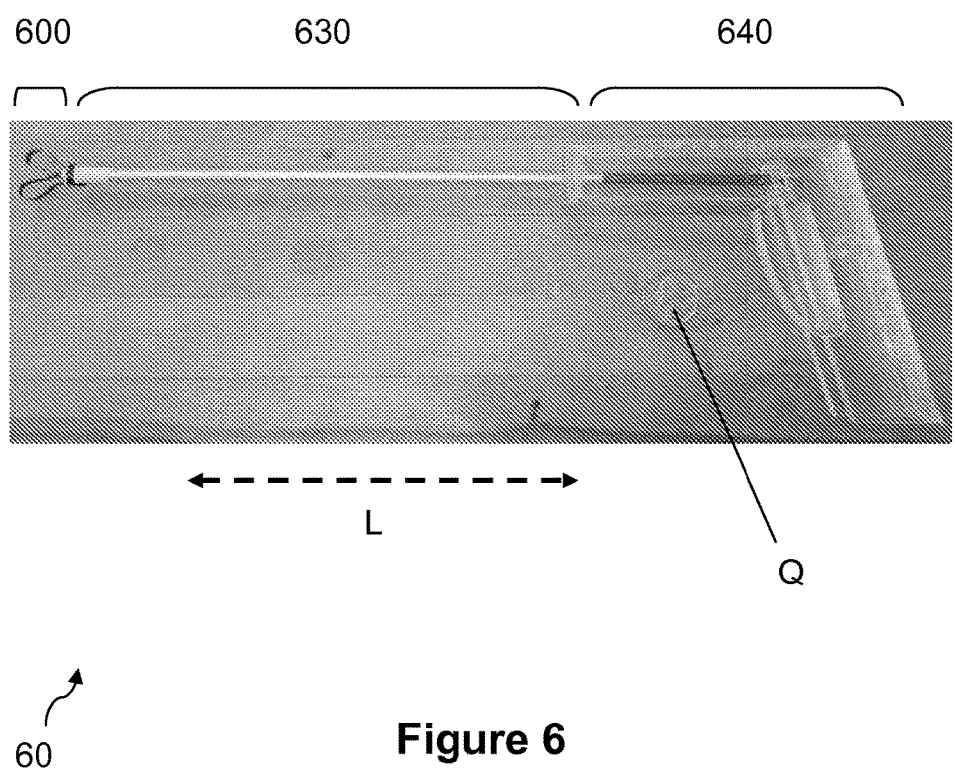
FIG. 6 is a simple endoscopic device that includes one embodiment of the atraumatic grasping arms described herein.

Those skilled in the art would understand that the grasping device described herein can be attached to the distal end of any type of endoscopic instrument and used in surgical procedures to grasp objects such as tissues or organs. Simply by way of example, a basic endoscopic grasper device 60 is shown in FIG. 6. In addition to a grasper device 600 described herein, an endoscopic grasper device 60 generally includes an elongate housing member 630 having a longitudinal axis L and a handle 640 at the proximal end. Simply for size perspective of this embodiment, a quarter Q is shown. In practice, endoscopic instruments can have a number of features such as, without limitation, ratcheting handle, joystick, rotatable control element, one or more rotatable jaws, and/or electrocautery. It should be understood that, while the endoscopic grasper device shown in FIG. 6 is a simple version and includes very few of the additional features indicated herein, any one or more of those features could be readily incorporated into one of the endoscopic grasper devices described herein.

An endoscopic grasper device as described herein can be provided in a variety of sizes, including different lengths as well as different diameters of the elongate housing member, depending on the specific intended application. Suitable dimensions of grasper devices as well as of the grasping arms themselves can vary dependent upon the particular endoscopic instrument, the type of surgery (e.g., laparoscopic), and/or the tissue or organs expected to be encountered during the procedure. The grasping arms described herein should be of a length that is sufficient to firmly grasp the desired object (e.g., tissue or organ). Suitable lengths of a grasper arm include, for example, from about 3 mm up to about 100 mm in length or greater. Simply by way of example, the length of the grasping arms for use with microsurgical tools can be from about 3 mm to about 7 mm (e.g., from about 3 mm to about 5 mm; from about 4 mm to about 6 mm; or from about 5 mm to about 7 mm). In addition, an exemplary length of the grasping arms for use with a laparoscopic instruments can be from about 10 mm up to about 50 mm (e.g., from about 20 mm to about 30 mm; from about 25 mm to about 35 mm; from about 30 mm to about 40 mm; or from about 35 mm to about 50 mm) Further, the length of the grasping arms for use with a general surgical instrument can be from about 50 mm up to about 100 mm or greater (e.g., from about 50 mm to about 75 mm; from about 60 mm to about 80 mm; from about 70 mm to about 90 mm; or about 75 mm to about 100 mm).

In certain instances, it may be useful to have a single compliant grasper arm as described herein opposite a non-compliant rigid arm or jaw. Non-compliant rigid arms or jaws are well known in the art as are the mechanisms for opening and closing such arms or jaws. See, for example, U.S. Pat. Nos. 5,538,008; 5,820,630; 5,906,630; 6,206,877; 6,964,662; and 7,494,501, as well as endoscopic graspers sold by, for example, Stryker, Inc. (Kalamazoo, Mich.), Ethicon (Somerville, N.J.), and Olympus (Tokyo, Japan).

The atraumatic grasping arms described herein can be used in a laparoscopic, thoracoscopic or other endoscopic procedures. Such procedures are well known in the art. As discussed herein, the endoscopic grasper device allows for atraumatic manipulation of an object such as tissue or an organ. Representative tissues and organs include, without limitation, stomach, intestinal, gall bladder, ovarian, vascular and lung tissue.

An endoscopic grasper device as described herein is introduced into a patient and the first and second grasping arms are actuated by the user to atraumatically manipulate the object. The grasping arms (e.g., at the distal end of the endoscope) can be introduced into a patient through a trocar sheath (e.g., 10 mm size). However, for non-laparoscopic procedures (e.g., general open surgical procedures), a trocar sheath may not be employed. During the insertion and positioning of the grasping arms, the arms usually are in a closed position to provide a narrow profile. The distal end of the device is then maneuvered to a desired position within a patient by a user grasping a handle. The user can open and close the grasping arms using any type of actuating means to manipulate the object (e.g., a tissue or organ). Although not required, locking means can be provided to lock the grasping arms in an open position and/or a closed position.

The compliant material used in the grasping arms also can include dimples or protrusions to further assist in manipulating, atraumatically, the object. In addition, micro-patterned treads, which have been shown to increase traction in wheeled in vivo robots (Sliker et al., 2010, J. Med. Devices, 4:041006), can be included on the graspers described herein. Therefore, this technology can be applied to the grasping arms described herein to increase the traction and pull force capabilities.

A grasper device described herein, with or without an endoscopic device, or an endoscopic grasper device described herein can be provided in a kit, which typically is packaged under sterile conditions. In some embodiments, more than one grasper device can be provided in a given sterile package. Packaging systems for medical devices are well known in the art. In addition, a grasper device described herein or an endoscopic grasper device described herein can be disposable or reusable. Reusable devices are those that can be used in multiple surgical procedures with sterilization treatments in between. Reusable devices provide substantial cost and waste savings relative to those that are disposed of after a single use.

In accordance with the present invention, there may be employed conventional engineering techniques and/or physiological techniques within the skill of the art. Such techniques are explained fully in the literature. The invention will be further described in the following examples, which do not limit the scope of the methods and compositions of matter described in the claims.

EXAMPLES

Example 1—Preliminary Methods

The grasper jaws were of uniform thickness, superelastic Nitinol ribbon (a biocompatible material) in order to achieve an evenly distributed grasping pressure on the tissue. Since the Nitinol is highly elastic, its deformation during closure around the tissue provided a means of distributing pressure on the tissue as opposed to pinching it in a localized portion of the jaw (e.g., at the tip). Nitinol was also selected for its shape-memory capabilities, which allowed the device to be easily fabricated. Heat treatment in a die was used to achieve the desired profile.

The design objective, illustrated in FIG. 1, was to achieve a compliant jaw profile that opens/closes through a central linear actuation resulting from a push/pull rod in a laparoscopic tool, without generating the tissue stress concentrations seen in rigid tool designs, even those that use compliant joints in their actuation.

By replacing rigid links and kinematic joints with compliant members, it was possible to utilize those unique compliance characteristics to transfer the push/pull actuation into jaw motion. This also imparted other advantages such as lower part count and reduced friction effects.

Thirteen different jaw profiles were modeled and analyzed to evaluate the motion achieved by linear displacement of the free end of the jaw. Once a profile demonstrated good kinematic performance (see, for example, FIG. 3), it was simulated grasping an oblong shape with properties similar to rubber to evaluate the uniformity of pressure distribution and the sharing of load between the tissue and the grasper itself.

For comparison purposes, a simplified standard laparoscopic grasper also was modeled and analyzed to show tissue stress concentrations, modeled as two stainless steel jaws rotated about a pivot point.

Example 2—Preliminary Results

Figure 4:
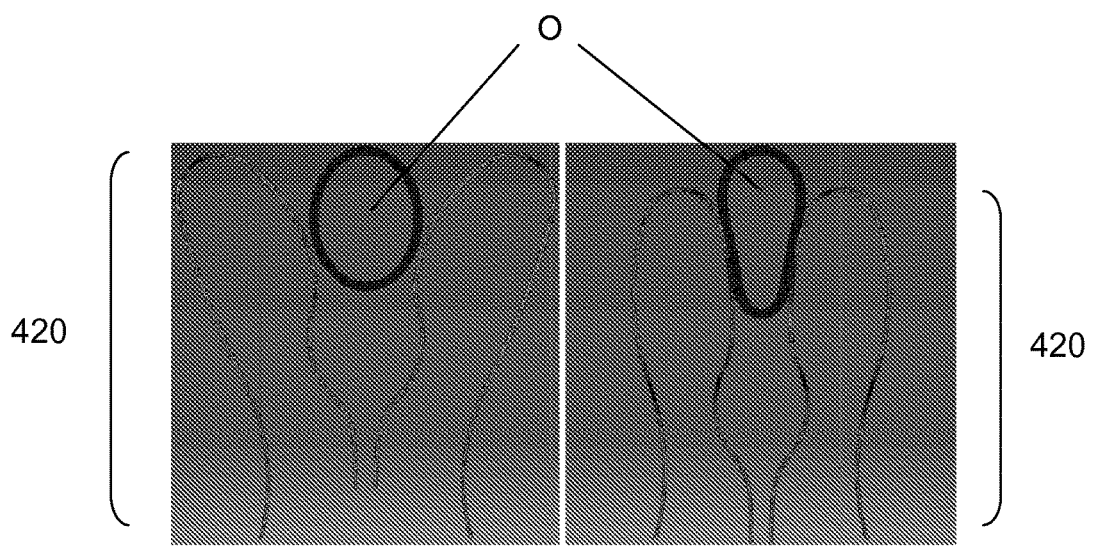
FIG. 4 is a schematic showing the effects on an object O of a compliant grasper as described herein in the open position (left panel) and closed position (right panel).
Figure 5:
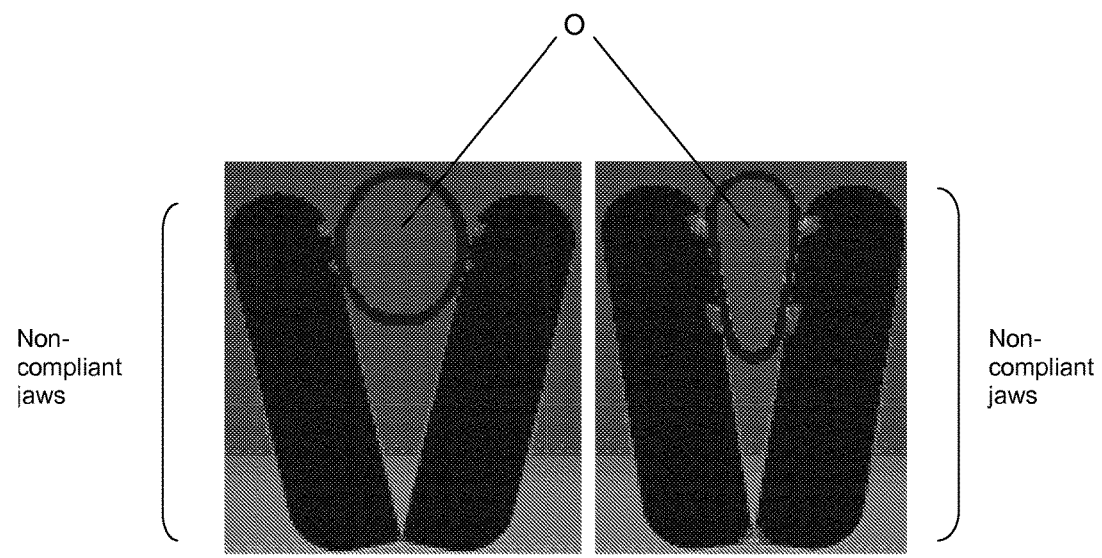
FIG. 5 is an image showing rigid graspers in an open position (left panel) and closing on an object O (right panel).

Upon examining the finite element method (FEM) results, it was seen in that a compliant jaw distributed pressure more evenly than a rigid jaw while providing grasp behavior sufficient to perform typical surgical manipulation tasks (FIGS. 4 and 5). The right panel of FIG. 4 shows appreciable jaw or grasper 420 deformation (the area in the lower part of the contact region) when grasping the tissue, thereby sharing the load and reducing stress locally on the tissue. FIG. 5 shows that the rigid jaws do not deform in this way and, thus, may create concentrated pressures on the specimen.

Example 3—Preliminary Grasper Design

A simple device was fabricated for testing purposes (FIG. 6), since the jaws were the area of focus. The grasper jaws, shown in FIG. 2, were made using Nitinol ribbon with a cross section of 3×0.2 mm, which was heat treated to induce the desired profile in the jaws. Extra features that often are found in commercial graspers were not included here, such as rotatable jaws and a ratcheting handle.

Actuation of the jaws was simplified such that squeezing the trigger laterally translated a push/pull rod through a pin-slot configuration at the top of the trigger, with the pivot position for the trigger being near the bottom of the handle. This lateral motion directly opened and closed the jaws by either pushing or pulling the inner legs of the jaw, causing the jaws to open or close, respectively, as seen in FIG. 2. The push rod was attached to the inner legs of the jaws, with the outer legs fixed to a stationary outer tube that enclosed the push rod. This caused the jaws to come together when the rod was pulled backwards. The jaws had a natural springback behavior due to the stored energy from deflection, so the jaws opened by themselves when the trigger was released (this default-open design is common in laparoscopic tools).

Example 4—Force Testing of the Preliminary Grasper Design

Two tests were performed to compare the compliant grasper described herein and a commercially available rigid grasper (AutoSuture™ EndoClinch™ II 5 mm, Mansfield, Mass.) with respect to pinch and pull force.

a) Pinch Force Test

Figure 7:
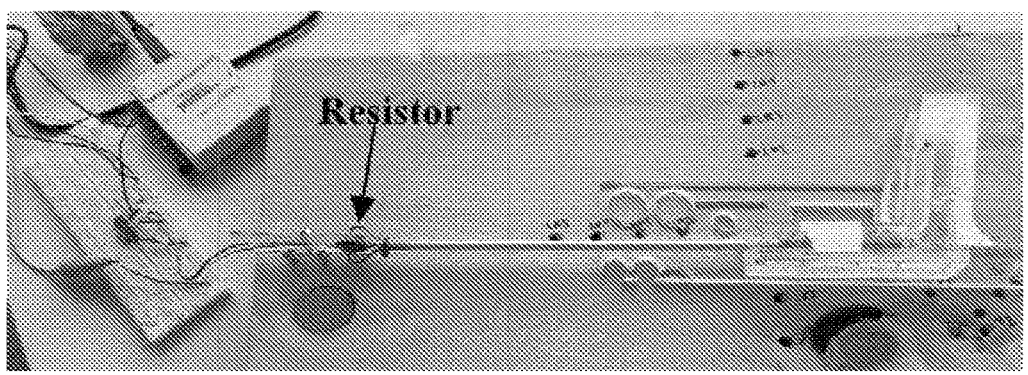
FIG. 7 is an image showing the pinch force test fixture for evaluating pinch forces.

A thin-film force sensitive resistor (FSR) was used to record pinch force data during testing. The graspers and resistor were fixed spatially (FIG. 7) so the jaws could clamp the sensor in the same location within the sensor's active area to ensure repeatability. A circuit with a +6V input was used based on the FSR manufacturer's recommendation to convert the pinch force seen by the sensor into an analog voltage signal read with an NI-DAQmx data acquisition device. Voltage data were then converted to force using a calibration curve.

b) Pull Force Test

Tests were performed to determine the maximum pull force the graspers were capable of producing. Porcine liver samples, 2×7×0.5 cm in size, were clamped in the grasper on one end, and weight was incrementally added on the other until the tissue slipped out of the jaws. Thirteen and nine trials were done with the compliant and rigid graspers, respectively, with new samples used for each trial.

Example 5—Results of the Force Testing a) Pinch Force

Figure 8:
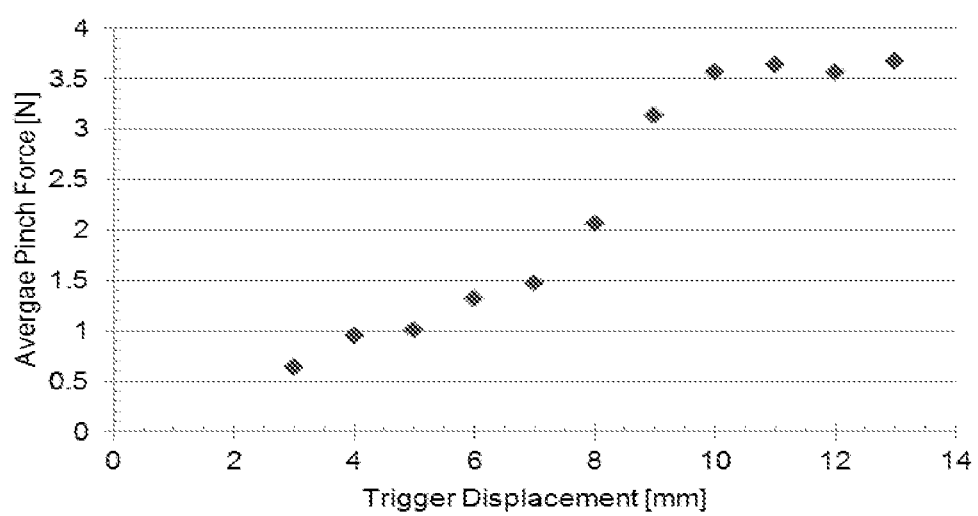
FIG. 8 is a graph showing the pinch force of the compliant grasper described herein.

Pinch force data for the compliant grasper were recorded as a function of the linear displacement of the push rod. The trigger was squeezed to translate the rod in 1 mm increments. FIG. 8 shows the relationship between the push rod displacement and the pinch force of the compliant grasper.

It was not possible to record the pinch force for the rigid grasper as a function of the displacement of its push rod since there was a considerable amount of play between the trigger, push rod and jaws due to the pin-in-slot joints at the jaws-and-rod and trigger-and-rod joints. The maximum pinch force of the rigid grasper was recorded over 10 trials with an average of 8.7 N.

b) Pull Force

The results for the pull tests are summarized in Table 1. For each trial, both graspers were closed as tight as possible to achieve the maximum pull force. In the case of the rigid grasper, which had 1 mm teeth, significant trauma was observed in the tissue samples following each trial.

TABLE 1

Pull test data

|  | Avg. Max. Pull Force [N] | Std. Dev. [N] |
|---|---|---|
| Compliant | 1.4 | 0.6 |
| Rigid | 8.1 | 0.8 |

Example 6—Analysis of Results

The pinch force data for the compliant grasper described herein shows an interesting and useful behavior. See FIG. 8. The relationship between the rod displacement and the pinch force was generally sigmoid in shape, with the initial portion being fairly linear, the steep rise around the 9 mm mark, and the plateau around 3.5N. The inherent maximum pinch force of the compliant grasper could prove to be useful in mitigating tissue trauma, and can be tailored by changing the geometric properties of the jaw.

It was observed during testing that, in the linear region, the contact area between the grasper and FSR sensor was increasing as the jaws closed around the sensor, and, at 9 mm of displacement, the jaws were fully in contact with the sensor. During the later stage of closure, the jaws also pulled the sensor towards the grasper as it pinched. This behavior was different than what was observed with the rigid grasper. Since the rigid jaws pivot at their base, the resulting grasping motion was a combination of pinching and pushing the sensor away from the grasper. This pinching/pushing behavior is counterintuitive to what would constitute efficient grasping since it moves the tissue in the opposite direction of the intended stretching.

It was expected that the compliant graspers would have an inferior maximum pull force compared to the rigid grasper since the interface between the jaws and tissue is toothless. However, it was found that the compliant graspers described herein should be able to achieve at least 5N of pull force without causing damage (based on methodology according to deVisser et al., 2002, Surg. Endosc., 16:1426-30).

It also was visually observed that the compliant graspers described herein caused minimal to no trauma to the tissue following each pull test trial, while significant damage (i.e., large perforations and torn tissue) was visually observed on samples grasped by the rigid graspers.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. An atraumatic grasper device, comprising:
   a base having a proximal end, a distal end, and a longitudinal axis extending therebetween, wherein the proximal end of the base is configured to be releasably attached to a distal end of an endoscopic instrument;
   a center member extending along the longitudinal axis of the base;
   a trigger coupled to the center member and configured to laterally translate the center member along the longitudinal axis,
   wherein the distal end of the base comprises:
      a first grasping arm and an opposing second grasping arm, wherein each of the first and the second grasping arms are made from a ribbon-shaped compliant material and comprise a first end and a second end and have a width of about 3 mm or greater, wherein the first end of the first grasping arm and the first end of the second grasping arm are positioned on the base distal to the longitudinal axis along a transverse axis and wherein the second end of the first grasping arm and the second end of the second grasping arm are positioned on the center member proximal to the longitudinal axis along the transverse axis, wherein either the first ends of the first and second grasping arms or the second ends of the first and second grasping arms are moveable along the longitudinal axis to actuate atraumatic grasping of an object between the first and second grasping arms by actuation of the trigger, such that when the trigger is pulled, the center member moves proximally causing the first grasping arm and the second grasping arm to move toward one another, and when the trigger is released, the center member naturally moves back to a neutral position causing the first grasping arm and the second grasping arm to move away from one another.

2. The device of claim 1, wherein the first and second grasping arms are made of shape memory alloy.

3. The device of claim 1, wherein the compliant material is elastic material.

4. The device of claim 1, wherein the second ends of the first and second grasping arms are moveable along the longitudinal axis.

5. An endoscopic grasper device comprising:
   an elongate housing member having a longitudinal axis and having a handle at a proximal end and opposing first and second grasping arms at a distal end;
   a center member extending along the longitudinal axis of the elongate housing member;
   a trigger coupled to the center member and configured to laterally translate the center member along the longitudinal axis,
   wherein each of the first and the second grasping arms are made from a ribbon-shaped compliant material and comprise a first end and a second end and have a width of about 3 mm or greater, wherein the first end of the first grasping arm and the first end of the second grasping arm are positioned on the elongate housing distal to the longitudinal axis along a transverse axis and wherein the second end of the first grasping arm and the second end of the second grasping arm are positioned on the center member proximal to the longitudinal axis along the transverse axis, wherein either the first ends of the first and second grasping arms or the second ends of the first and second grasping arms are moveable along the longitudinal axis to actuate atraumatic grasping of an object between the first and second grasping arms by actuation of the trigger, such that when the trigger is pulled, the center member moves proximally causing the first grasping arm and the second grasping arm to move toward one another, and when the trigger is released, the center member naturally moves back to a neutral position causing the first grasping arm and the second grasping arm to move away from one another.

6. The device of claim 5, wherein the first and second grasping arms are made of shape memory alloy.

7. The device of claim 5, wherein the compliant material is elastic material.

8. The device of claim 5, wherein the second ends of the first and second grasping arms are moveable along the longitudinal axis.

9. A method for atraumatically manipulating an object in an endoscopic procedure, comprising:
   (a) providing an endoscopic grasper device comprising an elongate housing member having a longitudinal axis and having a handle at a proximal end and opposing first and second grasping arms at a distal end, a center member extending along the longitudinal axis of the elongate housing member, a trigger coupled to the center member and configured to laterally translate the center member along the longitudinal axis, wherein each of the first and the second grasping arms are made from a ribbon-shaped compliant material and comprise a first end and a second end and have a width of about 3 mm or greater, wherein the first end of the first grasping arm and the first end of the second grasping arm are positioned on the elongate housing distal to the longitudinal axis along a transverse axis and wherein the second end of the first grasping arm and the second end of the second grasping arm are positioned on the center member proximal to the longitudinal axis along the transverse axis, wherein either the first ends of the first and second grasping arms or the second ends of the first and second grasping arms are moveable along the longitudinal axis to actuate atraumatic grasping of an object between the first and second grasping arms by actuation of the trigger, such that when the trigger is pulled, the center member moves proximally causing the first grasping arm and the second grasping arm to move toward one another, and when the trigger is released, the center member naturally moves back to a neutral position causing the first grasping arm and the second grasping arm to move away from one another; and (b) introducing the distal end of the endoscopic grasper device into a patient; and (c) actuating the first and second grasping arms to atraumatically manipulate an object.

10. The method of claim 9, wherein the first and second grasping arms are made of shape memory alloy.

11. The method of claim 9, wherein the compliant material is elastic material.

12. The method of claim 9, wherein the second ends of the first and second grasping arms are moveable along the longitudinal axis.

* * * * *